US00PP29103P2

(12) United States Plant Patent
Graff

(10) Patent No.: US PP29,103 P2
(45) Date of Patent: Mar. 13, 2018

(54) ***HIBISCUS* PLANT NAMED 'RHEA'**

(50) Latin Name: *Hibiscus rosa-sinensis*
Varietal Denomination: Rhea

(71) Applicant: Poul Graff, Sabro (DK)

(72) Inventor: Poul Graff, Sabro (DK)

(73) Assignee: Graff Breeding A/S, Sabro (DK)

( * ) Notice: Subject to any disclaimer, the term of this patent is extended or adjusted under 35 U.S.C. 154(b) by 0 days.

(21) Appl. No.: 15/530,657

(22) Filed: Feb. 16, 2017

(51) Int. Cl.
*A01H 5/02* (2006.01)

(52) U.S. Cl.
USPC ..... Plt./257

(58) Field of Classification Search
USPC ..... Plt./257
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Hibiscus* plant named 'Rhea', characterized by its upright, mounding and bushy plant habit; dark green-colored leaves; uniform and freely flowering habit; large bright orange-colored flowers with dark red-colored centers; excellent flower longevity; and relative resistance to bacterial leafspot.

3 Drawing Sheets

Botanical designation: *Hibiscus rosa-sinensis.*
Cultivar denomination: 'RHEA'.

BACKGROUND OF THE INVENTION

The present invention relates to a new and distinct cultivar of *Hibiscus* plant, botanically known as *Hibiscus rosa-sinensis*, and hereinafter referred to by the name 'Rhea'.

The new *Hibiscus* plant is a product of a planned breeding program conducted by the Inventor in Sabro, Denmark. The objective of the breeding program is to create new strong *Hibiscus* plants with attractive and long-lasting flowers.

The new *Hibiscus* plant originated from a cross-pollination in August, 2008 in Sabro, Denmark of a proprietary selection of *Hibiscus rosa-sinensis* identified as code designation GB 83x39 H.3, not patented, as the female, or seed, parent with a proprietary selection of *Hibiscus rosa-sinensis* identified as code designation GB 2007-0659, not patented, as the male, or pollen, parent. The new *Hibiscus* plant was discovered and selected by the Inventor as a flowering plant within the progeny of the stated cross-pollination in a controlled greenhouse environment in Sabro, Denmark in May, 2009.

Asexual reproduction of the new *Hibiscus* plant by vegetative terminal cuttings in a controlled greenhouse environment in Sabro, Denmark since September, 2010 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Rhea'.

These characteristics in combination distinguish 'Rhea' as a new and distinct *Hibiscus* plant:

1. Upright, mounding and bushy plant habit.
2. Dark green-colored leaves.
3. Uniform and freely flowering habit.
4. Large bright orange-colored flowers with dark red-colored centers.
5. Excellent flower longevity.
6. Relatively resistant to bacterial leafspot.

Plants of the new *Hibiscus* can be compared to plants of the female parent selection. Plants of the new *Hibiscus* differ primarily from plants of the female parent selection in the following characteristics:

1. Leaves of plants of the new *Hibiscus* are glossier than leaves of plants of the female parent selection.
2. Flowers of plants of the new *Hibiscus* are longer-lasting than flowers of plants of the female parent selection.
3. Plants of the new *Hibiscus* are more resistant to bacterial leafspot than plants of the female parent selection.

Plants of the new *Hibiscus* can be compared to plants of the male parent selection. Plants of the new *Hibiscus* differ primarily from plants of the male parent selection in the following characteristics:

1. Leaves of plants of the new *Hibiscus* are darker green in color than leaves of plants of the male parent selection.
2. Plants of the new *Hibiscus* are more freely flowering than plants of the male parent selection.
3. Flowers of plants of the new *Hibiscus* are longer-lasting than flowers of plants of the male parent selection.

Plants of the new *Hibiscus* can be compared to plants of the *Hibiscus rosa-sinensis* 'Adonis', disclosed in U.S. Plant Pat. No. 21,592. In side-by-side comparisons, plants of the new *Hibiscus* differ from plants of 'Adonis' in the following characteristics:

1. Flowers of plants of the new *Hibiscus* are long-lasting than flowers of plants of 'Adonis'.

2. Plants of the new *Hibiscus* and 'Adonis' differ in flower color as plants of 'Adonis' have dark pink-colored flowers.

Plants of the new *Hibiscus* can be compared to plants of the *Hibiscus rosa-sinensis* 'Boreas', disclosed in U.S. Plant Pat. No. 21,618. In side-by-side comparisons, plants of the new *Hibiscus* differ from plants of 'Boreas' in the following characteristics:

1. Plants of the new *Hibiscus* are not as vigorous as plants of 'Boreas'.
2. Plants of the new *Hibiscus* and 'Boreas' differ in flower color as plants of 'Boreas' have pale yellow-colored flowers.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet is a side perspective view of a typical flowering plant of 'Rhea' grown in a container.

The photograph on the second sheet is a close-up view of typical developing flower buds and a typical open flower of 'Rhea'.

The photograph on the third sheet is a close-up view of a typical dissected flower of 'Rhea' showing the upper surfaces of the petals.

DETAILED BOTANICAL DESCRIPTION

The aforementioned photographs and following observations, measurements and values describe plants grown during the autumn in 17-cm containers in a glass-covered greenhouse in Sabro, Denmark and under cultural practices typical of commercial *Hibiscus* production. During the production of the plants, day temperatures ranged from 20° C. to 25° C., night temperatures ranged from 19° C. to 21° C. and light levels ranged from 40 to 50 klux. Plants were pinched one time nine weeks after planting and plants were 26 weeks old when the photographs and the description were taken. In the description, color references are made to The Royal Horticultural Society Colour Chart, 2001 Edition, except where general terms of ordinary dictionary significance are used.

Botanical classification: *Hibiscus rosa-sinensis* 'Rhea'.

Parentage:

*Female, or seed, parent*.—Proprietary selection of *Hibiscus rosa-sinensis* identified as code number GB 83x39 H.3, not patented.

*Male or pollen parent*.—Proprietary selection of *Hibiscus rosa-sinensis* identified as code number GB 2007-0659, not patented.

Propagation:

*Type*.—By vegetative terminal cuttings.

*Time to initiate roots, summer*.—About three weeks at ambient and soil temperatures about 24° C.

*Time to initiate roots, winter*.—About four weeks at ambient and soil temperatures about 24° C.

*Time to produce a rooted young plant, summer*.—About eight weeks at ambient and soil temperatures about 24° C.

*Time to produce a rooted young plant, winter*.—About ten weeks at ambient and soil temperatures about 24° C.

*Root description*.—Medium in thickness, fleshy; color, close to 158A, actual color of the roots is dependent on substrate composition, water quality, fertilizer type and formulation, substrate temperature and physiological age of roots.

*Rooting habit*.—Freely branching; dense.

Plant description:

*Plant and growth habit*.—Container plant; upright, mounding and bushy plant habit; moderately vigorous growth habit.

*Branching habit*.—Freely branching habit with usually about four to six lateral branches developing per plant; pinching enhances lateral branch development.

*Plant height*.—About 35 cm to 55 cm.

*Plant diameter* (*area of spread*).—About 30 cm to 50 cm.

Lateral branch description:

*Length*.—About 5 cm to 25 cm.

*Diameter*.—About 3 mm to 6 mm.

*Internode length*.—About 1 cm to 5 cm.

*Strength*.—Strong.

*Texture*.—Smooth, glabrous; becoming woody with development.

*Color, developing*.—Close to 147A.

*Color, developed*.—Close to N199A.

Leaf description:

*Arrangement*.—Alternate, single; numerous.

*Length*.—About 8 cm to 12 cm.

*Width*.—About 6 cm to 10 cm.

*Shape*.—Broadly ovate.

*Apex*.—Acuminate.

*Base*.—Cordate, rounded.

*Margin*.—Irregularly serrate.

*Texture, upper surface*.—Smooth, glabrous; somewhat leathery.

*Texture, lower surface*.—Scattered pubescence; venation prominent.

*Luster, upper and lower surfaces*.—Moderately glossy.

*Venation pattern*.—Pinnate; arcuate.

*Color*.—Developing leaves, upper surface: Close to 136B. Developing leaves, lower surface: Close to 137B. Fully expanded leaves, upper surface: Close to N189A; venation, close to N138A. Fully expanded leaves, lower surface: Close to 136B; venation, close to 139B.

*Petioles*.—Length: About 2 cm to 5 cm. Diameter: About 2 mm. Texture, upper and lower surfaces: Pubescent. Color, upper surface: Close to 139A. Color, lower surface: Close to 147A.

*Leaf stipules*.—Quantity and arrangement: Two at the base of the petiole, opposite. Length: About 5 mm. Diameter: About 1 mm. Shape: Lanceolate. Color, upper and lower surfaces: Close to 199A.

Flower description:

*Flower arrangement*.—Flowers arranged singly at terminal leaf axils; uniform, continuous and freely flowering habit with numerous flowers developing per plant; flowers face mostly upright to slightly outwardly.

*Fragrance*.—None detected.

*Natural flowering season*.—Plants flower in the garden during the spring and summer or during periods of warm weather; in the greenhouse, plants can be flowered year-round; plants begin flowering about 12 to 16 weeks after pinching.

*Flower longevity*.—Excellent flower longevity, flowers last for about four to five days; flowers persistent.

*Flower diameter*.—About 12 cm to 19 cm.

*Flower length* (*height*).—About 8 cm to 9 cm.

*Flower buds*.—Rate of opening: Flowers buds open in about three days. Length: About 5 cm to 7 cm. Diameter: About 1.5 cm to 3 cm. Shape: Ovoid to elliptical. Aspect: Mostly upright. Color: Close to N34C.

*Petals*.—Arrangement: Five petals in a single whorl; petals imbricate. Length: About 8 cm to 10 cm. Width: About 6 cm to 8 cm. Shape: Fan-shaped. Apex: Rounded. Base: Attenuate. Margin: Entire; slightly undulate. Texture, upper surface: Glabrous; rough with a velvety appearance. Texture, lower surface: Glabrous, rough with a satiny appearance. Luster, upper surface: Matte. Luster, lower surface: Slightly glossy. Color: When opening, upper surface: Close to 28B; towards the base, close to 53A. When opening, lower surface: Close to 29A. Fully opened, upper surface: Close to N30B; towards the base, close to 46B; with development, main color becoming closer to 28A and towards the base, close to 53B; venation, close to 54C. Fully opened, lower surface: Close to 30B; towards the base, close to 64D; with development, color becoming closer to 29A and towards the base, close to 35B; venation, close to 29A.

*Sepals*.—Appearance: Five sepals fused into a campanulate-shaped calyx. Length: About 3 cm to 4 cm. Width: About 1 cm to 1.5 cm. Shape: Lanceolate. Apex: Acuminate. Margin: Entire. Texture, upper surface: Glabrous, rough. Texture, lower surface: Glabrous, smooth. Color, upper surface: Close to 143A. Color, lower surface: Close to 143C.

*Peduncles*.—Length: About 3 cm to 5 cm. Diameter: About 3 mm to 4 mm. Strength: Strong. Aspect: Mostly upright. Texture: Sparsely pubescent. Color: Close to 137A.

*Involucral bracts*.—Quantity and arrangement: About six in a single whorl subtending the calyx and forming a star-shaped epicalyx. Length: About 1 cm to 1.5 cm. Diameter: About 2 mm to 5 mm. Shape: Lanceolate. Apex: Acute. Margin: Entire. Texture, upper and lower surfaces: Rough, glabrous. Color, upper and lower surfaces: Close to 147A.

*Reproductive organs*.—Androecium: Stamen number: Numerous, more than 100. Filament length: About 3 mm. Filament color: Close to 47C. Anther shape: Round to ovate. Anther length: About 1 mm to 2 mm. Anther color: Close to 20A. Amount of pollen: Abundant. Pollen color: Close to 20A. Gynoecium: Pistil length: About 6 cm to 8 cm. Staminal column texture: Smooth, waxy. Staminal column color: Close to 47C; towards the base, close to 53A. Style length: Five-parted, about 5 mm to 6 mm. Style color: Close to 4C. Stigma appearance: Five rounded stigma pads. Stigma pad color: Close to 44A. Ovary color: Close to 4C.

*Seeds*.—To date, seed production has not been observed on plants of the new *Hibiscus*.

Temperature tolerance: Plants of the new *Hibiscus* have been observed to have tolerate temperatures from about 10° C. to about 40° C.

Pathogen & pest resistance: Plants of the new *Hibiscus* have been observed to relatively resistant to bacterial leafspot (*Xanthomonas campestris* and *Phytomonas syringae*). Plants of the new *Hibiscus* not been observed to be resistant to pests and other pathogens common to *Hibiscus* plants.

It is claimed:

1. A new and distinct *Hibiscus* plant named 'Rhea' as illustrated and described.

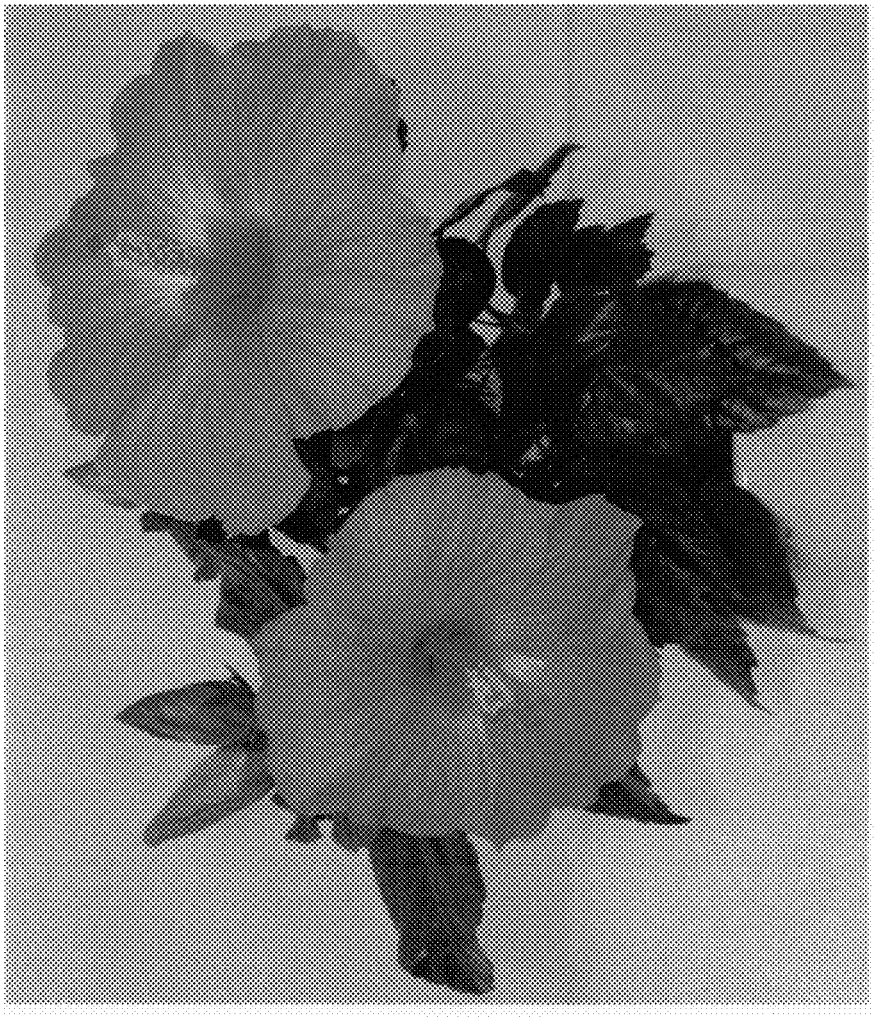

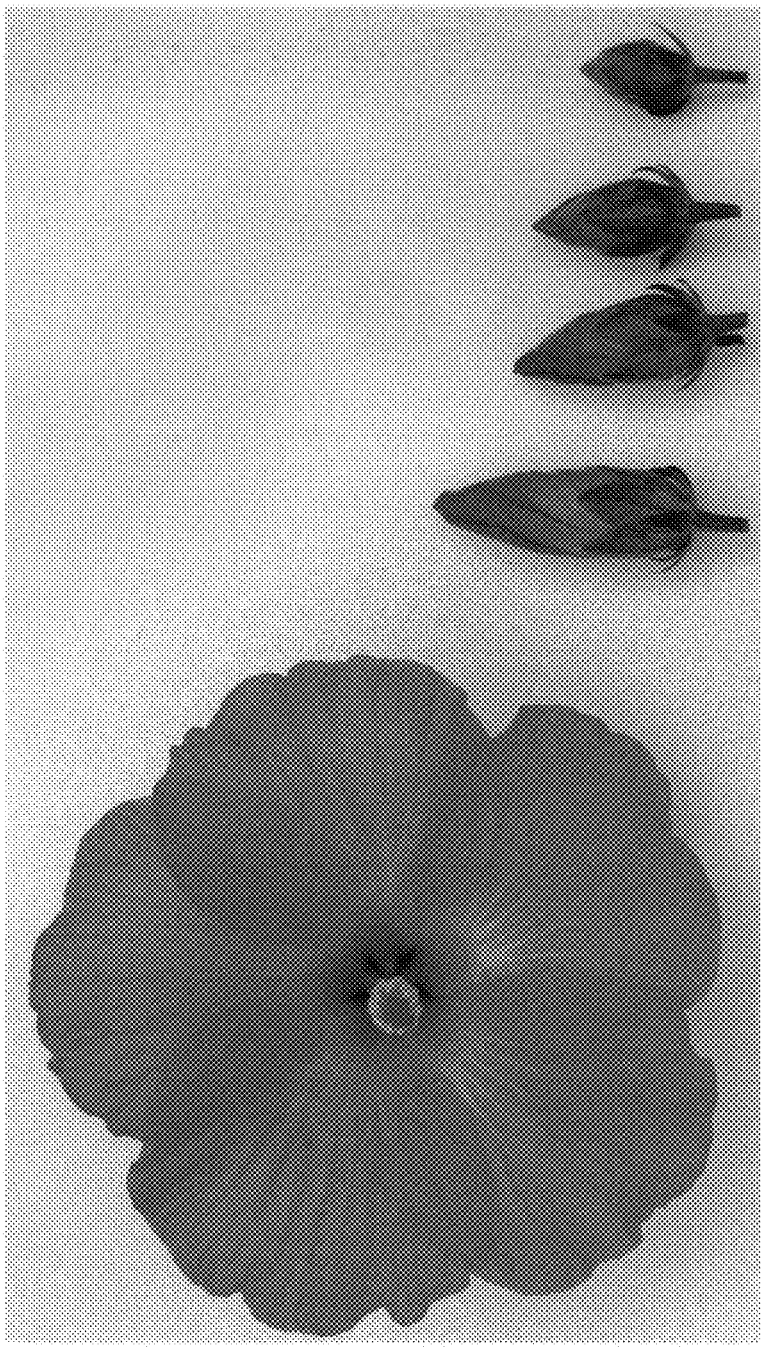

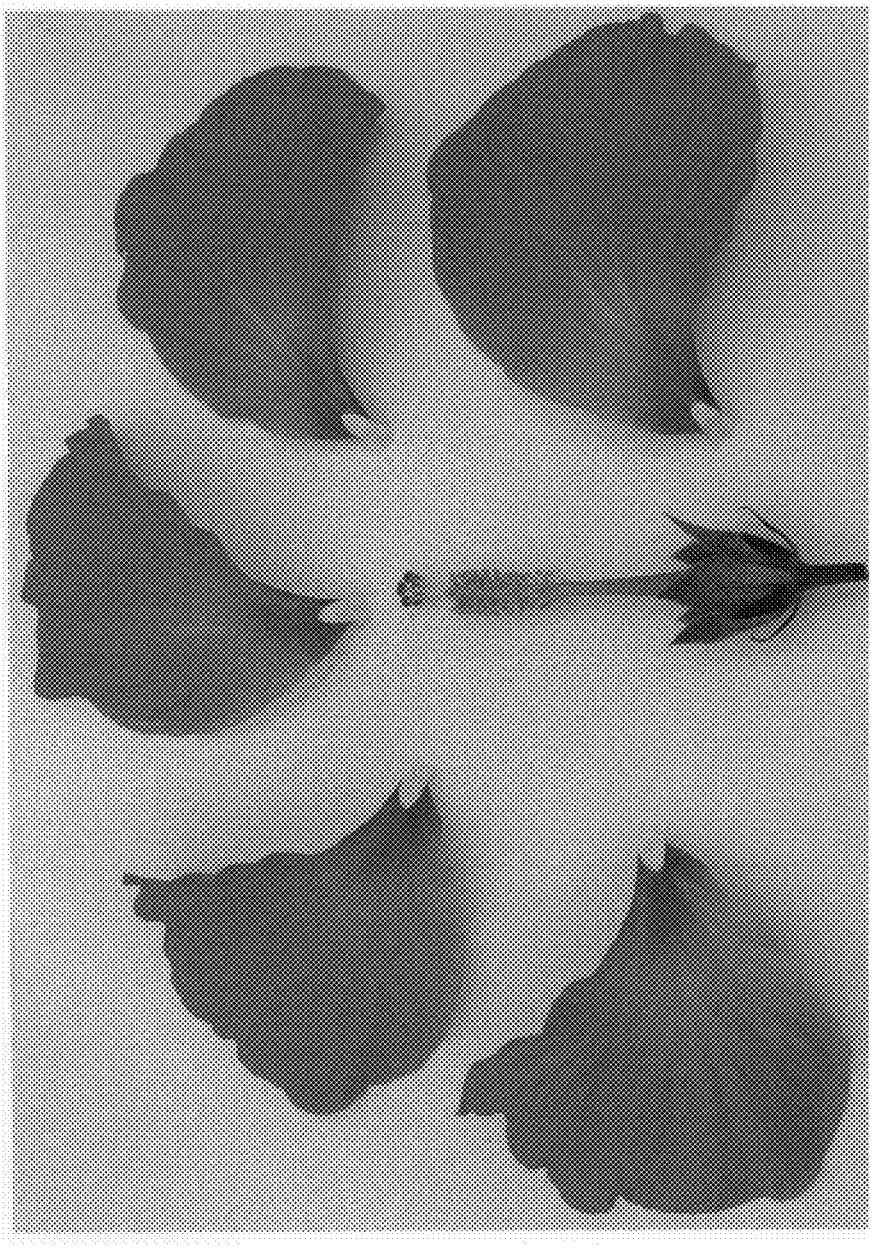

* * * * *